United States Patent [19]

Heller

[11] Patent Number: 4,502,976
[45] Date of Patent: Mar. 5, 1985

[54] WATER SOLUBLE POLYESTERS

[75] Inventor: Jorge Heller, Woodside, Calif.

[73] Assignee: Bend Research, Inc., Bend, Oreg.

[21] Appl. No.: 436,284

[22] Filed: Oct. 25, 1982

[51] Int. Cl.$^3$ .............................................. B01J 13/00
[52] U.S. Cl. ........................... 252/315.4; 428/402.24;
   524/916; 560/204; 528/222; 528/300; 528/303
[58] Field of Search ................ 252/315.4; 428/402.24;
   524/916

[56] References Cited

U.S. PATENT DOCUMENTS 3,444,091  5/1969  Petraglia ........................ 252/315.4

Primary Examiner—Lucille M. Phynes
Attorney, Agent, or Firm—Chernoff, Vilhauer, McClung, Birdwell & Stenzel

[57] ABSTRACT

Water-soluble polyesters useful in the preparation of bioerodible hydrogels are described. The polyesters are formed by condensing three monomers: a first monomer which is either an unsaturated aliphatic or cycloaliphatic dicarboxylic acid or an unsaturated aliphatic or cycloaliphatic diol; a second monomer which is a water-soluble polyglycol; and a third monomer which is a dicarboxylic acid having an electron-withdrawing group placed vicinally to a carbonyl group of the acid. Water-soluble polyesters with molecular weights ranging from about 5000 to about 30,000 are disclosed.

4 Claims, No Drawings

WATER SOLUBLE POLYESTERS

DESCRIPTION

1. Technical Field

This invention relates to water soluble polyesters useful in the preparation of bioerodible hydrogels. The hydrogels are suitable carriers for water-soluble therapeutic macromolecules, and when the hydrogels carrying such macromolecules are implanted in living mammals they degrade, releasing the macromolecules and forming water-soluble degradation fragments which are eliminated in the course of normal functions of the host mammals.

2. Background Art

Controlled release methodologies are known and can be broadly classified into diffusional, osmotic, and erosional depending upon the mechanism which controls the release of the therapeutic agent. In the case of macromolecular therapeutic agents, diffusional release through dense polymeric membranes is not possible due to the large size of these therapeutic agents.

While it is possible to dispense macromolecules with osmotic devices, they are complex, bulky, and nonerodible so that systemic drug delivery from an implant site requires first surgical implantation and subsequently surgical removal of the expended device.

Attempts have been made to dispense therapeutic macromolecules from hydrogels, but because the bioerosion rate of the hydrogels heretofore proposed, such as hydrogels prepared by copolymerization of N,N'-methylene-bisacrylamide and various water-soluble monomers, is extremely slow, very poor control over the rate of macromolecule delivery has been achieved. Thus, as shown by the work of Torchilin and co-workers described in J. Biomed. Mater Res., 11, 223-231 (1977), only hydrogels containing less than 1 weight percent crosslinker are bioerodible and macromolecule release from such loosely crosslinked hydrogels occurs largely, if not solely, by diffusion, and almost 50% of the entrapped macromolecule is released in the first day of utilization.

It is the object of this invention to provide means for producing hydrogels that contain linkages labile enough so that adequate crosslink density to fully immobilize the entrapped macromolecule can be used and yet the resulting hydrogel will bioerode at useful rates and gradually release the entrapped macromolecule as the hydrogel gradually bioerodes.

It is a further object of this invention to prepare hydrogels where the rate of bioerosion can be manipulated by structural variations of the hydrogel so that the rate of release of the entrapped macromolecule can be adjusted to values dictated by the specific applications.

DISCLOSURE OF INVENTION

Pursuant to the invention, water-soluble polyesters having molecular weights preferably in the range of about 5000 to 30,000 are formed by condensing 3 monomers. The first monomer is either an unsaturated aliphatic or cycloaliphatic dicarboxylic acid or an unsaturated aliphatic or cycloaliphatic diol. The second monomer is a water-soluble polyglycol, and the third monomer is a dicarboxylic acid having an electron-withdrawing group placed vicinally to a carbonyl group of the acid. The total number of hydroxyl groups of the monomers employed is substantially equal to the total number of carboxyl groups of the monomers employed.

The lower alkyl esters of the acid monomers may be employed instead of the acids themselves in which case the water-soluble polymers are formed by transesterification rather than by direct esterification.

Where the first monomer employed is an unsaturated dicarboxylic acid, the water-soluble polyester has the following generalized formula:

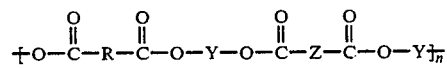

When the first monomer employed is an unsaturated diol then the polymer has the following generalized formula:

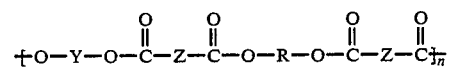

In the above formula R is an unsaturated lower aliphatic or cycloaliphatic group, Y is a water-soluble polyglycol group, and Z is a dicarboxylic acid nucleus having an electron-withdrawing group placed vicinally to a carbonyl group of the acid.

In preparing the polyesters, the monomers, one containing an R group, one containing a Y group, and one containing a Z group, are mixed and a small amount of an esterification catalyst, such as para-toulenesulfonic acid or sodium methoxide, is added. The mixture is then flushed with nitrogen or argon to remove oxygen, and is heated to temperatures in the range about 130° C. to 180° C., usually for several hours, during which the esterification reaction proceeds to completion. In some cases propylene glycol is added to increase the yield of polyester. A vacuum (typically 2 mm Hg) is used to remove any propylene glycol present and to remove water or lower alkanols produced by the esterification or transesterification reaction, respectively.

Suitable monomers containing an R group which provides the necessary unsaturation in the finished polyester include fumaric acid, 1-hexane-1,6-dioic acid, 2,5-dimethyl-3-hexene-1,6-dioic acid, 3-heptene-1,7-dioic acid, 2-pentene-1,5-dioic acid, 2-cyclohexene-1,4-dioic acid, 2-butene-1,4-diol, 2-pentene-1,5-diol, 3-hexene-1,6-diol, 2-hexene-1,6-diol, 2-butene-1,4-dimethyl-1,4-diol, allylmalonic acid, and itaconic acid.

Suitable monomers providing the Y group which provides the necessary water solublity to the finished polyester are the polyglycols, particularly polyethylene glycols ranging in molecular weight from about 200 to about 1000, preferably from 500 to 700, and polyglycols prepared by condensing ethylene glycol and propylene glycol so long as the amount of propylene glycol included does not have an appreciable adverse effect on water solubility.

Suitable monomers providing the Z group which has the effect of increasing the rate of hydrolysis of the finished polymer include diglycolic acid, 2-ketoglutaric acid, ketomalonic acid, and dicarboxylic acids having halogen atoms bonded to the nuclear portion of the acid such as perfluorosuccinic acid.

The monomer mixtures are so made that the number of terminal hydroxyl groups in the glycol monomers is essentially equal to the number of carboxyl groups in the dicarboxylic acid monomers, which results in essentially a neutral polyester.

The molar ratio of R-containing monomers and Z-containing monomers may be varied to control the rate of hydrolysis of the finished polymer. The ratio of R monomers to Z monomers may be varied usually within the range 4 to 1 through 1 to 4, the rate of hydrolysis of the finished polymer being greater when the proportion of Z monomers is greater than the proportion of R monomers.

In the second of the above formulas the only acid monomer shown is the acid containing the Z group. Since this acid increases rate of hydrolysis it will frequently be desirable to mix the Z-type acid with a saturated dicarboxylic acid such as butanedioic acid, pentanedioic acid, hexanedioic acid and the like in amounts from about 20 percent to 80 percent. The mixtures provide the carboxyl groups necessary for esterification and the reduced Z-type acid contained in the mixture increases the hydrolysis rate of the water-soluble polyester product but to a lesser extent than the rate increase which would be obtained if only the Z-type acid were used.

The unsaturated water-soluble polyesters are converted to hydrogels by connecting the linear chains by covalent bonds formed by reactions of the unsaturated groups in the water-soluble polyester.

It is advantageous to form such covalent links by either connecting the linear chains through the double bonds using free-radical initiators or by initiating free-radical polymerization of water-soluble monomers in the presence of the unsaturated water-soluble polyester so that a copolymerization process takes place that connects the water-soluble polyester by short chains of the polymerized water-soluble monomer.

Macromolecular therapeutic agents are readily incorporated into the polymer to form bioerodible masses of polymer in which the therapeutic agent is entrapped by carrying out the polymerization reaction of the dissolved monomers in the presence of the dissolved macromolecule. Such a process is particulary advantageous because it is carried out at essentially room temperature in water at an essentially neutral pH so that even the most sensitive macromolecules can be safely entrapped in the hydrogel without any danger of loss of activity due to denaturing. When these masses are implanted in a mammal, slow hydrolysis of the polymer mass occurs with continuous slow release of the therapeutic material at a locus in the mammal at which its function is required.

To form these masses the macromolecular therapeutic agent is dissolved in a buffer solution which is close to the neutral point. An appropriate amount of the polyester prepared as described above is dissolved in the buffer solution, which is then stripped of any contained oxygen by bubbling nitrogen or argon through it. A crosslinking agent, such as N-vinylpyrrolidone or acrylamide, is then added to the solution. Crosslinking is initiated by adding a small amount of a redox catalyst, such as ammonium peroxydisulfate. The crosslinking reaction proceeds rapidly, and can be made more rapid by addition of an accelerator, such as ferrous ammonium sulfate or N,N,N',N'-tetramethylethylenediamine. The crosslinked polymer containing entrapped thereapeutic material can then be put into any desired form; for example, it may be poured onto a glass plate and the water evaporated, leaving the film of entrapped therapeutic agent or it may be dispersed in hexane or other organic solvent and agitated with the result that microspheres of the entrapped therapeutic agent are formed. The microspheres may be injected into a mammal requiring treatment.

DETAILED DESCRIPTION OF THE INVENTION

In the following examples detailed descriptions of the preparation of the water-soluble polyesters of the invention are provided and their use in incorporating macromolecules in the polymer are described.

EXAMPLE 1

0.1642 mols of polyethylene glycol having a molecular weight range from about 570 to 630 (sold by Union Carbide under the trade name "CARBOWAX 600"), 0.1610 mols of fumaric acid and 24.5 milligrams of hydroquinone were placed in a round-bottom flask equipped with a distillation condenser and the flask was purged with nitrogen to remove all contained oxygen. The hydroquinone serves to inhibit polymerization of fumaric acid during the polyesterification reaction.

Heating of the flask was commenced and the heating device was set for a maximum of 190° C. At the end of a half hour the 190° C. temperature was reached and solution of the components in the flask in each other became complete. Water was distilled out of the flask reaction. Heating was continued for six hours during which a viscous, clear, greenish yellow liquid formed in the flask. The product was a water-soluble polyester.

Bovine serum albumin was entrapped in this polymer by crosslinking the polymer with N-vinylpyrrolidone in the presence of the bovine serum albumin. The erosion rate of this polymer was very slow and approximately 20% of the bovine serum albumin was released over a period of one month.

The polymer of this example contained only two monomers, the fumaric acid and the polyethylene glycol, and no monomer containing an electron-withdrawing group was present. This polymer has utility in instances in which very slow erosion is required with release of the contained macromolecule occurring at a very slow rate over a long period.

EXAMPLE 2

0.2 mols of the polyethylene glycol used in Example 1, 0.1 mols of fumaric acid, and 0.1 mols of diglycolic acid were placed in a round-bottom flask as in Example 1. 0.24 mols of propylene glycol were added to aid the esterification process. 0.165 grams of hydroquinone and 0.826 grams of para-toluenesulfonic acid were added and the flask was flushed with argon. Heating was commenced and during the first hour of heating the temperature rose to 130° C. After two hours of additional heating the temperature was raised to 150° C. and the reaction mixture was held at that temperature overnight. The following morning the temperature was raised to 180° C. and the flask was placed under vacuum until all of the propylene glycol had distilled out of the reaction mixture. The product was a pale yellow, clear, viscous polyester.

EXAMPLE 3

A polyester was prepared following the procedure of Example 2 and using the monomers of Example 2, but using the fumaric acid and diglycolic acids in amounts such that the molar ratio of diglycolic acid to fumaric acid was 3 to 2.

The polyester was a clear, viscous material having a slightly yellowish color.

EXAMPLE 4

A polyester was prepared using the monomers and the procedure of Example 2 but the molar ratio of diglycolic acid to fumaric acid in the material charged to the flask was 4 to 1. The polyester was a clear viscous material of pale yellow color.

The polyesters of Examples 3 and 4 hydrolyze more readily than the polymer of Example 2 due to their higher content of diglycolic acid.

EXAMPLE 5

0.180 mols of polyethylene glycol of the type used in the preceding examples, 0.09 mols of fumaric acid, and 0.09 mols of 2-ketoglutaric acid were placed in a round-bottom flask as in the preceding examples. 0.216 mols of propylene glycol, 0.03 grams of hydroquinone, and 0.749 grams of para-toluenesulfonic acid were also added to the flask. The flask was then flushed with argon and over a period of two hours the temperature of the flask and contents was raised to 150° C. and the flask was then left at that temperature overnight. The following morning the temperature was raised to 180° C., a vacuum was applied to the flask and the propylene glycol and water were distilled off. 126.3 grams of polyester in the form of a clear, viscous, yellowish liquid were obtained as product.

EXAMPLE 6

A polyester was prepared using the materials and procedure set out in Example 5 but the molar ratio of ketoglutaric acid to fumaric acid employed in this example was 1 to 4. The polymer product, containing, as it did, a lesser amount of ketoglutaric acid than the polymer of Example 5, was slower to undergo hydrolysis.

EXAMPLE 7

0.030 mols of diethylketomalonate, 0.0225 mols of polyethylene glycol having a molecular weight of 610 and 0.0090 mols of 2-butenediol were charged to a round-bottom flask. 3.95 milligrams of hydroquinone and 19.7 grams of sodium methoxide were added to this mixture. The flask was then flushed with argon and heating was commenced. The temperature was raised to 140° C. during the first half hour and then was taken to 156° C. Heating was continued to 4 hours and during the last hour and one-half of heating a vacuum was applied to remove all traces of ethanol produced.

The polyester product was a dark, reddish brown, syrupy liquid which was soluble in both water and acetone.

EXAMPLE 8

0.05 mols of polyethylene glycol of molecular weight 610, 0.06 mols of propylene glycol, 0.025 mols of fumaric acid, 0.025 mols of perfluorosuccinic acid, 8.5 milligrams of hydroquinone and 214 milligrams of para-toluenesulfonic acid were placed in a round-bottom flask. The flask was flushed with argon. Over a period of two hours the temperature of the flask and contents was brought to 130° C. After three hours at 130° C. the temperature was raised to 150° C. and the flask and contents were held at that temperature overnight. The following morning the temperature was raised to 180° C. and a vacuum was applied to the flask to remove the propylene glycol and the last traces of water vapor. The polyester product was a colorless, clear, viscous material.

EXAMPLE 9

In all of the foregoing examples the double bond of fumaric acid or of butenediol, whichever was used, became a part of the backbone of the polyester. We discovered, however, that if the double bond is pendent from the polymer backbone rather than a part of it, crosslinking of the polyester is facilitated and smaller amounts or perhaps no crosslinking agent are required. This example as well as Example 10 illustrates the use of this principle.

0.2 mols of polyethylene glycol of molecular weight about 610, 0.24 mols of propylene glycol, 0.10 mols of itaconic acid, and 0.1 mols of ketoglutaric acid were charged to a round-bottom flask. 0.168 grams of hydroquinone and 1.68 milliliters of para-toluenesulfonic acid were added to this mixture. The flask was flushed with argon. The mixture was heated to 180° C. and maintained at this temperature for six hours. During the last two hours of heating a vacuum was applied to remove propylene glycol and produced water. 145.4 grams of polyester product were obtained.

EXAMPLE 10

0.06 mols of polyethylene glycol of molecular weight about 600, 0.07 mols of propylene glycol, 0.06 mols of diethylallylmalonate, 0.01 grams of hydroquinone and 0.27 grams of para-toluenesulfonic acid were charged to a round-bottom flask. The flask was flushed with argon, heating was commenced at 110° C., and the temperature was taken to 150° C. over a period of six hours. The following day the flask was taken to 180° C. and a vacuum was applied to remove produced ethanol and the propylene glycol. A polyester product was obtained which was a faintly turbid, pale yellow, viscous liquid.

The pendent double bonds contained in the polyesters produced in Examples 9 and 10 provide the required unsaturation to the polymers and these polyesters are more readily crosslinked than the polyesters in which the double bond forms a part of the polymer backbone.

The following table lists several additional representative monomer mixtures which may be condensed to form water-soluble polyesters pursuant to the invention:

| Monomer | Molar Parts of Monomer |
|---|---|
| 1. Fumaric Acid | 1 |
| Polyethylene Glycol | 2 |
| Diglycolic Acid | 1 |
| 2. Butenediol | 1 |
| Polyethylene Glycol | 2 |
| Ketoglutaric Acid | 3 |
| 3. Butenediol | 1 |
| Polyethylene Glycol | 2 |
| Ketoglutaric Acid | 1 |
| Butanedioic Acid | 2 |
| 4. Itaconic Acid | 1 |
| Polyethylene Glycol | 2 |
| Ketomalonic Acid | 1 |
| 5. Fumaric Acid | 1.5 |
| Polyethylene Glycol | 2.0 |
| Diglycolic Acid | 0.5 |
| 6. Allylmalonic Acid | 1.25 |
| Polyethylene Glycol | 2.0 |
| Ketoglutaric Acid | 0.75 |

The following Examples 11, 12, and 13 describe the use of the water-soluble polyesters set forth above to form bioerodible hydrogels in which macromolecules are incorporated. Bovine serum albumin is used as a model macromolecule. Other macromolecular materials such as antigens, hormones, and the like having a therapeutic function may be similarly incorporated in the hydrogels.

EXAMPLE 11

Bovine serum albumin was incorporated into the polymer of Example 2 according to the following procedure. Two grams of that polymer were weighed in a 100 milliliter beaker and dissolved in 5 milliliters of 0.1 M pH 7.4 phosphate buffer containing 0.5 wt % bovine serum albumin. For a typical formulation with 40 wt % crosslinking agent, 800 milligrams of N-vinylpyrrolidone was then added along with 0.1 milliliter of 0.1 wt % ferrous ammonium sulfate, 1 milliliter of 1 M tris buffer at pH 8.6 and 1 milliliter of a 1.12 wt % aqueous solution of N,N,N',N'-tetramethylethylethylene-diamine. Oxygen was removed from the solution by bubbling nitrogen through it for 20 minutes. The polymerization was then initiated by adding 1 milliliter of a nitrogen-purged 0.5 wt % aqueous solution of ammonium peroxydisulfate.

The resulting 10–12 milliliters of solution was thoroughly agitated for a few seconds and then poured onto a glass plate. Four shims of the desired thickness were then placed at the four corners of the glass plate and a second glass plate placed on top of the shims. The glass plates were next placed in an oven at 35° C. for 30 minutes, the plates removed, disassembled, and the film removed and washed in water to remove unreacted monomer. The film was then cut to the desired shapes and sizes and was ready for use.

EXAMPLE 12

Bovine serum albumin was also incorporated into the polymer of Example 11 and prepared in the form of small beads according to the following procedure. A polymerization mixture identical to that described in Example 11 was prepared and then added dropwise to 100 milliliters of rapidly stirred n-hexane containing 4 milliliters of sorbitan sesquioleate (a surfactant sold by I.C.I. Chemicals under the trademane "Arlacel C"). The system was then brought to 37° C. on a water bath and maintained at that temperature for 30 minutes with continued stirring and under a nitrogen purge. The microparticles were then partially dehydrated by an addition of 100 milliliters of absolute ethanol, the hexane was decanted off, and the solution was vacuum filtered and dried overnight in a vacuum desiccator over anhydrous $P_2O_5$.

Very fine, uniform, and free-flowing particles were obtained. To use in mammals, they can be resuspended in saline and injected with a 22-gauge hypodermic needle.

EXAMPLE 13

Bovine serum albumin was incorporated into the polymer of Example 10 according to the following procedure. Because pendent unsaturated groups are capable of undergoing a free-radical crosslinking reaction, no vinyl monomer such as N-vinylpyrrolidone is used. Five grams of polymer of Example 10 were weighed into a 100 milliliter beaker and dissolved in 5 milliliters of 0.1 M pH 7.4 phosphate buffer containing 0.5 wt % bovine serum albumin. Next, 1 milliliter of 0.1 wt % ferrous ammonium sulfate, 1 milliliter of 1 M tris buffer at pH 8.6 and 1 milliliter of a 1.12 wt % aqueous solution of N,N,N',N'-tetramethylethylenediamine were added, and oxygen was removed from the solution by bubbling nitrogen through it for 30 minutes. The polymerization was then initiated by adding 1 milliliter of a nitrogen-purged 12.5 wt % aqueous solution of ammonium peroxydisulfate. Sheets of crosslinked polymer could be prepared as described in Example 11 or microspheres could be prepared as described in Example 12.

When the polymers of the invention are crosslinked to encapsulate therapeutic macromolecules, the rate of bioerosion can be controlled by two means. First, the bioerosion rate, which is essentially dependent on the hydrolysis rate, can be controlled in part by varying the molar ratio of the Z monomer to R monomer when the polymer is prepared. The higher the ratio of Z monomer to R monomer the more rapid will be the hydrolysis rate and also the more rapid will be the bioerosion rate. Second, the bioerosion rate may also be controlled by varying the amount of crosslinking agent used in crosslinking the polymer. As the amount of crosslinking is increased, the rate of bioerosion is decreased. Thus, if the weight of the crosslinking agent such as N-vinylpyrrolidone or acrylamide is equal to or greater than the weight of the polymer, the bioerosion rate of the crosslinked material is greatly reduced.

Bovine serum albumin was incorporated into polyesters made from ketoglutaric acid, fumaric acid and polyethylene glycol. The ratios of ketoglutaric acid to fumaric acid of the polymers studied were 1 to 1, 2 to 3, and 1 to 4. All of the polymers had been crosslinked with an equal amount by weight of N-vinylpyrrolidone. When the ratio of ketoglutaric acid to fumaric acid was 1 to 1, 50% of the bovine serum albumin had been released from the crosslinked polymer at the end of 34 days. When the ratio of ketoglutaric acid to fumaric acid was 2 to 3, 50% of the bovine serum albumin had been released from the crosslinked polymer at the end of 51 days. When the ratio of ketoglutaric acid to fumaric acid was 1 to 4, 50% of the bovine serum albumin had been released from the crosslinked polymer at the end of 90 days. Clearly, bioerosion of the crosslinked polymer is more rapid when the quantity of ketoglutaric acid relative to the quantity of fumaric acid in the polymer is high.

Polymers of ketoglutaric acid, fumaric acid, and polyethylene glycol in which the ratio of ketoglutaric acid to fumaric acid was 4 to 1 were crosslinked with N-vinylpyrrolidone using varying amounts of crosslinking agent. When the weight of crosslinking agent employed was 20% of the weight of the polymer being crosslinked, then 50% of the bovine serum albumin had been released from the crosslinked polymer at the end of 4 days. When the weight of crosslinking agent was 40% of the weight of the polymer being crosslinked then 50% of the bovine serum albumin had been released at the end of 7 days. When the weight of crosslinking agent used was 60% of the weight of the polymer being crosslinked then 50% of the bovine serum albumin had been released at the end of 9 days. When the weight of crosslinking agent employed was equal to 100% of the weight of the polymer being crosslinked then 50% of the bovine serum albumin had been released at the end of 17 days. From this study of the effect of the amount of crosslinking agent used on the bioerosion rate of the crosslinked polymer, it is clear that as the amount of crosslinking agent is increased the bioerosion rate is decreased.

These polymers may be made suitable for delivery of low-molecular-weight agents by bioerosion or by diffusion followed by bioerosion. In this case, the polyesters should include a high number of closely spaced unsaturated groups, which result in a tightly crosslinked polymer. This might be accomplished, for example, by using polyglycols of molecular weight about 300 together with ratios of R monomer to Z monomer greater than 4 to 1.

The water-soluble polyesters of the present invention can be crosslinked in an aqueous medium containing therapeutic macromolecules with the result that the therapeutic macromolecule is encapsulated in the crosslinked polymer. The rate of release of the therapeutic agent can be controlled by adjusting the ratio of the R monomer to the Z monomer used in the preparation of the polymer and by varying the amount of crosslinking agent employed during the encapsulation of the macromolecule.

I claim:

1. Polyesters useful in the preparation of bioerodible hydrogels having the general formula

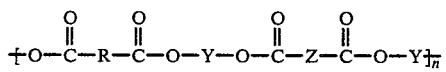

in which R is an unsaturated lower aliphatic or cycloaliphatic group, Y is a water-soluble polyglycol group, Z is a dicarboxylic acid nucleus having an electron-withdrawing group placed vicinally to a carbonyl group of the acid, and n is an integer such that the molecular weight of the polyester is in the range about 5000 to about 30,000.

2. Polyesters useful in the preparation of bioerodible hydrogels having the general formula

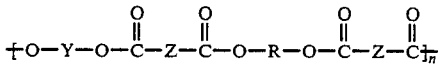

in which R is an unsaturated lower aliphatic or cycloaliphatic group, Y is a water-soluble polyglycol group, Z is a dicarboxylic acid nucleus having an electron-withdrawing group placed vicinally to a carbonyl group of the acid, and n is an integer such that the molecular weight of the polyester is in the range about 5000 to about 30,000.

3. Polyesters useful in the preparation of bioerodible hydrogels in which the monomer precursors of the polymer are one or more of the group consisting of fumaric acid and butenediol; one or more of the group consisting of diglycolic acid, ketoglutaric acid, ketomalonic acid, and fluorosuccinic acid; and a water-soluble polyglycol, the monomers being used in proportions such that the total number of terminal hydroxyl groups of the monomers employed is substantially equal to the total number of carboxyl groups contained in the acid monomers employed.

4. Polyesters useful in the preparation of bioerodible hydrogels formed by esterifying a mixture of an unsaturated aliphatic or cycloaliphatic diol, a water-soluble polyglycol, a dicarboxylic acid having an electron-withdrawing group placed vicinally to a carbonyl group, and a lower aliphatic dicarboxylic acid, the proportion of the components of the mixture being such that the total number of terminal hydroxyl groups of the components is essentially equal to the number of terminal carboxyl groups of the components.

* * * * *

UNITED STATES PATENT AND TRADEMARK OFFICE
CERTIFICATE OF CORRECTION

PATENT NO. : 4,502,976
DATED : March 5, 1985
INVENTOR(S) : Jorge Heller

It is certified that error appears in the above-identified patent and that said Letters Patent is hereby corrected as shown below:

Col. 2, line 51    Change "solublity" to --solubility--

Col. 7, line 46    Change "trademane" to --trade name--

Signed and Sealed this

Twelfth Day of August 1986

[SEAL]

Attest:

DONALD J. QUIGG

*Attesting Officer*    *Commissioner of Patents and Trademarks*